United States Patent [19]

Chang

[11] Patent Number: 4,695,408

[45] Date of Patent: Sep. 22, 1987

[54] PREPARATION OF TRISPHENOL METHANES

[75] Inventor: Kuo Y. Chang, Midland, Mich.

[73] Assignee: The Dow Chemical Company, Midland, Mich.

[21] Appl. No.: 751,342

[22] Filed: Jul. 2, 1985

[51] Int. Cl.$^4$ ............................................. C09B 11/06
[52] U.S. Cl. .................................................... 260/395
[58] Field of Search ........................................ 260/395

[56] References Cited

U.S. PATENT DOCUMENTS

| | | | |
|---|---|---|---|
| Re. 31,467 | 12/1983 | Jones et al. | 260/395 |
| 877,053 | 1/1908 | Conzetti | 260/395 |
| 950,359 | 2/1910 | Weiler et al. | 260/395 |
| 1,004,610 | 10/1911 | Weiler et al. | 260/395 |
| 1,707,181 | 3/1929 | Weiler et al. | 260/395 |
| 2,116,827 | 5/1938 | Foldi | 260/395 |
| 3,449,418 | 6/1969 | Werner | 260/395 |
| 3,579,542 | 5/1971 | Meyer et al. | 260/395 |
| 3,739,000 | 6/1973 | Lodolini et al. | 260/391 |
| 3,787,451 | 1/1974 | Mah | 260/348 |
| 4,048,200 | 9/1977 | Tresper et al. | 260/395 |
| 4,394,496 | 7/1983 | Schrader | 528/98 |

OTHER PUBLICATIONS

Chemical Abstracts 68:12811g, 1968.
Beilstein EII6, pp. 1111–1112, EIV6, pp. 7630–7631, pp. 7643–7644.

*Primary Examiner*—Glennon H. Hollrah
*Assistant Examiner*—Raymond Covington
*Attorney, Agent, or Firm*—Paul D. Hayhurst

[57] ABSTRACT

Prepare tris(p-hydroxy-disubstituted phenyl) methanes from 2,6-disubstituted phenols and salicylaldehyde.

17 Claims, No Drawings

PREPARATION OF TRISPHENOL METHANES

BACKGROUND OF THE INVENTION

The present invention relates to a process for the preparation of trisphenol methanes.

Certain pharmaceutical hydroxyl-containing triaryl methanes and their preparation are disclosed in U.S. Pat. No. Re. 31,467. Other generic references to triaryl methane compounds include U.S. Pat. Nos. 877,053; 3,449,418; 3,739,000; and 4,048,200. It is generally well-known that trisphenolics can be prepared by condensing an alkoxy-substituted aromatic aldehyde or an alkoxy-substituted aromatic ketone with an excess of a substituted or unsubstituted phenol. See, e.g., U.S. Pat. Nos. 2,116,827; 3,787,451; and 4,394,496. U.S. Pat. No. 3,579,542 teaches the preparation of 4,4',4"-trihydroxy-triphenylmethyl methane by condensing p-hydroxyacetophenone with phenol using a metal halide or acid catalyst. It is also known to react salicylaldehyde with certain phenolic compounds to obtain 4,4',2"-trihydroxyphenyl methanes. See, e.g., Beilstein EII6, pp. 1111–2; EIV6, pp. 7630–1; and EIV6, pp. 7643–4.

It is known to prepare a 4,4',4"-methylidyne tris(2,6-dimethylphenol) by reacting ethyl orthoformate (triethoxy methane) with the magnesium bromide Grignard reagent of 2,6-dimethylphenol. Chemical Abstracts 68:12811g. Said method employs relatively expensive starting materials, and requires special care since Grignard reagents react rapidly with both water and oxygen.

Heretofore, 4,4',4"-methylidyne tris(2,6-dimethylphenol) and related tris(p-hydroxyphenyl)methanes have not been prepared from the relatively inexpensive salicylaldehyde and its derivatives.

SUMMARY OF THE INVENTION

The present invention is a process comprising contacting a 2,6-disubstituted phenol with salicylaldehyde under reaction conditions such that a tris-(4-hydroxy-3,5-disubstituted phenyl)methane is formed. Surprisingly, the tris(p-hydroxyphenyl) product is obtained without using a p-hydroxyphenyl ketone or aldehyde as a starting material. The tris-(4-hydroxy-3,5-disubstituted phenyl)methanes are useful chemical intermediates, and can be converted to tris epoxy resins using known methods.

DETAILED DESCRIPTION OF THE INVENTION

The process of the present invention advantageously employs a 2,6-disubstituted phenol and salicylaldehyde.

A 2,6-disubstituted phenol desirably having a boiling point higher than the boiling point of phenol is advantageously employed in the process of the present invention. The 2,6-disubstituted phenol can have a wide variety of substituents so long as they do not prevent the reaction. Examples of typical substituents include halo, hydrocarbyl, substituted hydrocarbyl, H, alkoxy and aryloxy. Preferred substituents include alkyl of up to about 10 carbon atoms. More preferred substituents are n-alkyl. The most preferred 2,6-disubstituted phenol is 2,6-dimethylphenol. Mixtures of these phenols can be employed, and the 2- and 6-substituents can be different. The substituents preferably are such that phenol can be easily separated from the reaction mixture using known separation techniques, such as distillation.

The 2,6-disubstituted phenol can be employed in any amount which will give the desired product. Typically, the molar ratio of the 2,6-disubstituted phenol to salicylaldehyde is from about 3 to about 10, and preferably is from about 4 to about 6.

The contacting of salicylaldehyde and the 2,6-disubstituted phenol can occur under any set of reaction conditions which give the desired product. Preferably, the reactants are contacted in a distillation column reactor under any combination of conditions sufficient to distill the phenol overhead. Typical temperatures range from about 42° C. to about 120° C. and preferably are from about 60° C. to about 90° C. The pressure typically is from about 2 mm Hg to about 100 mm Hg, and preferably is from about 6 mm Hg to about 30 mm Hg.

A catalyst is optionally employed in the process of the present invention, and can be any material which catalyzes the reaction. Examples of typical catalysts include acid catalysts such as mineral acids, organic acids such as p-toluene sulfonic acid, and solid acids such as acidic ion-exchange resins. Mixtures of catalysts can be employed. When employed, the catalyst is employed in a catalytic amount. Preferably, the catalyst is employed in an amount such that the ratio of acid equivalents to starting salicylaldehyde is from about 0.05 to about 0.2.

When salicylaldehyde and a 2,6-disubstituted phenol are contacted as described hereinabove, a tris-(4-hydroxy-3,5-disubstituted phenyl)methane is produced. Preferred product compounds are represented by the formula:

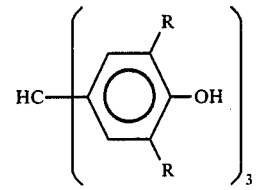

wherein each R independently is halo, hydrocarbyl or substituted hydrocarbyl. The R moieties are defined by the substituents on the 2,6-disubstituted phenol.

SPECIFIC EMBODIMENTS

The following example is given to illustrate the invention and should not be construed as limiting its scope.

EXAMPLE 1

A mixture of 188.8 g of 2,6-dimethylphenol and 69.5 g of salicylaldehyde is stirred and heated at 118° C. in the presence of 3.0 g of toluene sulfonic acid monohydrate for 24 hours. Then, an additional 30.4 g of 2,6-dimethylphenol is added to the mixture, and the resulting mixture is distilled at a pressure of 180–200 mm Hg in a 20-plate distillation column having a diameter of about one inch to remove 35 g of phenols overhead. The material in the distillation pot is poured into 600 ml of room temperature methanol. The methanol solution is seeded with an authentic 4,4',4"-methylidyne tris(2,6-dimethylphenol) and is allowed to stand overnight. The resulting crystals are collected by filtration and are washed with fresh methanol and then are dried in air to give 25 g of orange crystals having a nuclear magnetic resonance spectrum identical to that of an authentic sample.

What is claimed is:

1. A process comprising contacting a 2,6-disubstituted phenol with salicylaldehyde under reaction conditions such that there is formed a product represented by the formula:

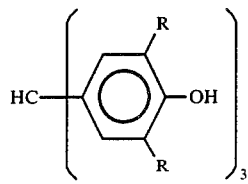

wherein each R independently is alkoxy, aryloxy, or alkyl of up to about 10 carbon atoms; or H or halo.

2. A process of claim 1 wherein each R independently is alkyl of up to about 10 carbon atoms.

3. A process of claim 2 wherein each R independently is n-alkyl of up to about 10 carbon atoms.

4. A process of claim 3 wherein at least one R is methyl.

5. The process of claim 1 wherein the contacting is conducted in the presence of a catalyst.

6. A process of claim 5 wherein the catalyst is an acid catalyst.

7. A process of claim 6 wherein the catalyst is toluene sulfonic acid or a hydrate thereof.

8. The process of claim 1 wherein the contacting is conducted at a temperature of from about 42° C. to about 120° C.

9. A process of claim 1 wherein each R is identical.

10. A process of claim 3 wherein at least one R is ethyl.

11. The process of claim 1 wherein from about 3 to about 10 moles of the 2,6-disubstituted phenol are employed per mole of salicylaldehyde.

12. The process of claim 1 wherein from about 4 to about 6 moles of 2,6-disubstituted phenol are employed per mole of salicylaldehyde.

13. A process comprising contacting 2,6-dimethylphenol with salicylaldehyde in the presence of a catalyst under reaction conditions such that there is formed a compound of the formula:

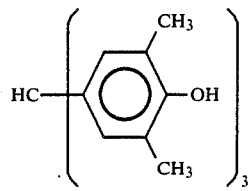

14. A process of claim 13 wherein the catalyst is an acid catalyst.

15. A process of claim 13 wherein the catalyst is toluene sulfonic acid or a hydrate thereof.

16. A process comprising contacting 2,6-dimethyl phenol and salicylaldehyde in the presence of an acid catalyst under distillation reaction conditions such that there is formed tris-(4-hydroxy-3,5-dimethylphenyl)methane.

17. A process of claim 16 wherein the catalyst comprises toluene sulfonic acid or a hydrate thereof.

* * * * *